(12) United States Patent
Lai (10) Patent No.: US 9,943,219 B2
(45) Date of Patent: Apr. 17, 2018

(54) MULTIDIRECTIONAL FOOT CONTROLLER

(71) Applicant: HIWIN TECHNOLOGIES CORP., Taichung (TW)

(72) Inventor: Dong-Gu Lai, Taichung (TW)

(73) Assignee: Hwin Technologies Corp., Taichung (TW)

( * ) Notice: Subject to any disclaimer, the term of this patent is extended or adjusted under 35 U.S.C. 154(b) by 299 days.

(21) Appl. No.: 14/793,079

(22) Filed: Jul. 7, 2015

(65) Prior Publication Data

US 2017/0007218 A1 Jan. 12, 2017

(51) Int. Cl.
| | | |
|---|---|---|
| *A61B 17/00* | (2006.01) | |
| *G05G 1/36* | (2008.04) | |
| *A61B 1/00* | (2006.01) | |
| *G05G 1/42* | (2008.04) | |
| *A61B 34/00* | (2016.01) | |
| *A61B 34/30* | (2016.01) | |

(52) U.S. Cl.
CPC ...... *A61B 1/00149* (2013.01); *A61B 1/00039* (2013.01); *A61B 34/74* (2016.02); *G05G 1/36* (2013.01); *G05G 1/42* (2013.01); *A61B 2017/00973* (2013.01); *A61B 2034/301* (2016.02)

(58) Field of Classification Search
CPC ........ G05G 1/42; G05G 1/36; A61B 1/00149; A61B 17/00234; A61B 17/00
See application file for complete search history.

(56) References Cited

U.S. PATENT DOCUMENTS

| | | | | | |
|---|---|---|---|---|---|
| 4,965,417 | A | * | 10/1990 | Massie | H01H 21/26 200/86.5 |
| 5,983,749 | A | * | 11/1999 | Holtorf | G05G 1/30 74/478 |
| 6,452,123 | B1 | * | 9/2002 | Chen | G05G 1/30 200/86.5 |
| 6,786,502 | B2 | * | 9/2004 | Carlson | A63C 5/128 280/14.22 |
| 7,058,998 | B2 | | 6/2006 | Diller et al. | |
| 7,185,555 | B2 | * | 3/2007 | Peterson | G05G 1/30 74/512 |
| 8,749,188 | B2 | * | 6/2014 | Tran | H01H 21/26 200/86.5 |
| 2002/0137007 | A1 | * | 9/2002 | Beerstecher | A61C 1/0023 433/101 |

(Continued)

FOREIGN PATENT DOCUMENTS

WO    WO 96/13845    *  5/1996

OTHER PUBLICATIONS

Define immovable—Google Search, google.com., Dec. 27, 2017.*

*Primary Examiner* — Vinh Luong
(74) *Attorney, Agent, or Firm* — Muncy, Geissler, Olds & Lowe, P.C.

(57) ABSTRACT

A multidirectional foot controller includes a base, a first platform, a second platform, and two pedals successively stacked and assembled together. The multidirectional foot controller is activated by having the two pedals depressed simultaneously, and then controls an externally connected endoscope to move forward or backward by a first platform, or controls the endoscope to move leftward or rightward by a second platform. By having only one of the pedals depressed, the multidirectional foot controller can change the field of view of the endoscope.

7 Claims, 6 Drawing Sheets

(56) References Cited

U.S. PATENT DOCUMENTS

| | | | |
|---|---|---|---|
| 2005/0172404 A1* | 8/2005 | Diller | A61G 13/02 5/616 |
| 2006/0145540 A1* | 7/2006 | Mezhinsky | A61F 9/00745 307/119 |

* cited by examiner

MULTIDIRECTIONAL FOOT CONTROLLER

BACKGROUND OF THE INVENTION

1. Technical Field

The present invention relates to foot controllers, and more particularly to a multidirectional foot controller suitable for positioning an endoscope.

2. Description of Related Art

In the process of minimally invasive surgery using endoscope, for fast adjustment of the endoscope's field of view, while keeping the endoscope stable, a robotic arm is typically employed to provide structural support to the endoscope. The operating surgeon operates a foot controller to move the robotic arm that in turn places the endoscope as needed.

Such a foot controller, as disclosed in U.S. Pat. No. 7,058,998, may use plural buttons to activate different functions. However, the known device has some of the buttons provided on the same panel, and tends to lead to users' wrong stepping. Furthermore, since some of the buttons are located near edges of the controller's base, it is likely that the user's foot slips off the keys and failed operation is caused. Hence, the prior-art device needs to be improved for better operational convenience and stability.

BRIEF SUMMARY OF THE INVENTION

The primary objective of the present invention is to provide a multidirectional foot controller, which allows multidirectional operation, while providing good operational stability and accuracy.

To achieve the foregoing objective, the disclosed multidirectional foot controller comprises a base, two first position detecting switches, two second position detecting switches, a first platform, a second platform, and two pedals. The two first position detecting switches are located at front and rear ends of the base. The two second position detecting switches are located at left and right sides of the base. The first platform is such slidably installed on the top surface of the base so that it can move forward or backward with respect to the base. When the first platform moves to the end of its travel, it touches one of the first position detecting switches, and starts to control a robotic arm to drive an endoscope to move forward or backward. The second platform is such pivotally installed on the top surface of the first platform so that it can rotate leftward or rightward with respect to the first platform. When the second platform to the end of its rotational range, it touches one of the second position detecting switches, and starts to control the robotic arm to drive the endoscope to move leftward or rightward. The two pedals are tandem arranged on the top surface of the second platform, for a user to depress and thereby make the first platform move forward or backward and make the second platform to rotate leftward or rightward.

Thereby, the disclosed multidirectional foot controller can use the first platform to move the endoscope forward or backward, and use the second platform to move the endoscope leftward or rightward. Additionally, the endoscope's field of view can be sized by the user's stepping on a single. The resultant multidirectional operation helps to improve working efficiency and operational stability.

In one embodiment of the present invention, the base has a lower housing, an third platform, and at least two rollers. The third platform is placed on the top surface of the lower housing. The two rollers are arranged at two ends of the third platform. The two first position detecting switches are located at front and rear ends of the lower housing. The two second position detecting switches are located at left and rear sides of the lower housing. The first platform is stacked on the top surface of the third platform. The first platform has its bottom surface provided with at least two roller tracks. Each of the roller tracks abuts against one said roller. Thereby, the first platform can slide forward or backward on the base in virtue of the rollers.

In one embodiment of the present invention, the first platform has its top surface provided with a first pivot portion. The second platform has its bottom surface provided with a second pivot portion. The first and second pivot portions are pivotally connected through a bearing, so that the second platform can rotate leftward or rightward with respect to the first platform. In addition, a torsion spring is provided between the second platform and the first platform, so that the second platform after intended rotation can be returned to its initial position by the torsion spring.

In one embodiment of the present invention, the first platform has a lower curved groove, and the second platform has an upper curved groove. The upper and lower curved grooves jointly receive a guiding member passing therethrough. The guiding member has one end fixed to the second platform, so that the second platform can move more stably with the support from the guiding member.

DETAILED DESCRIPTION OF THE INVENTION

Figure 1:
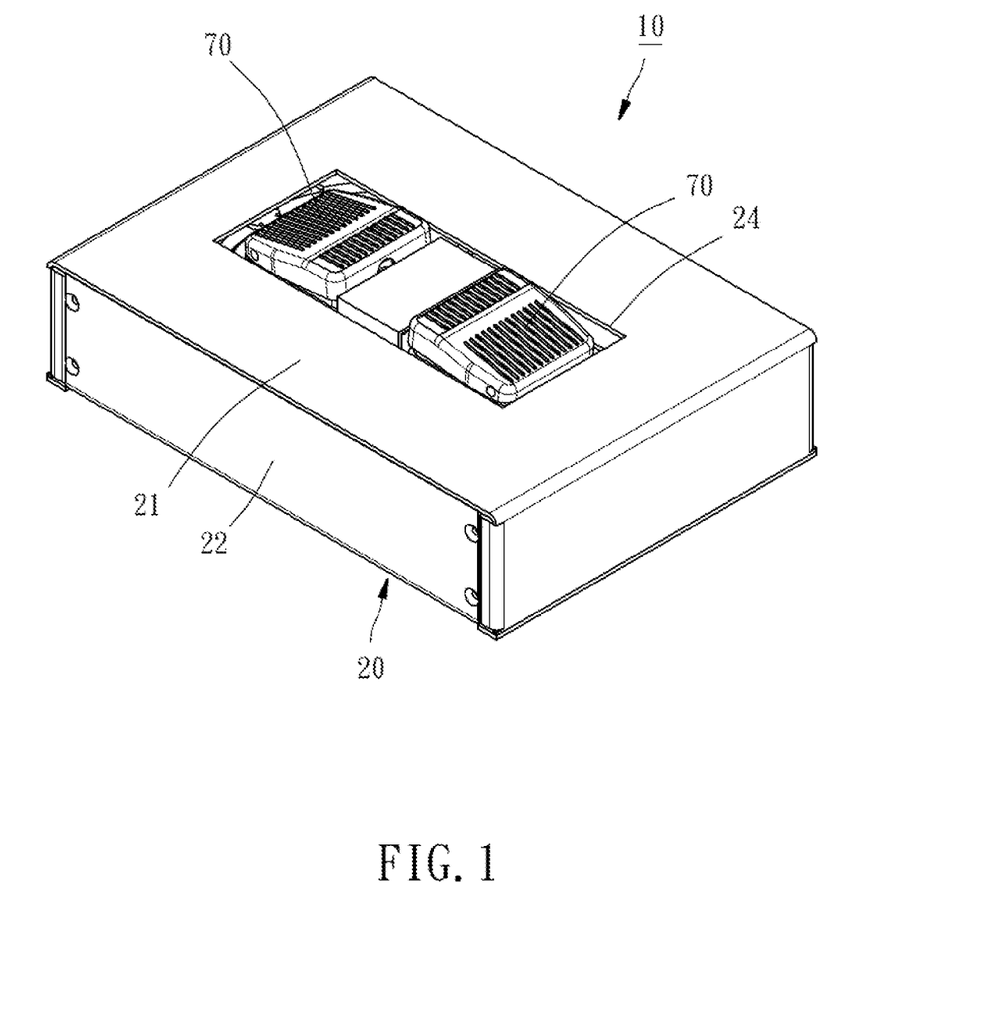
FIG. 1 is a perspective view of the present invention.
Figure 2:
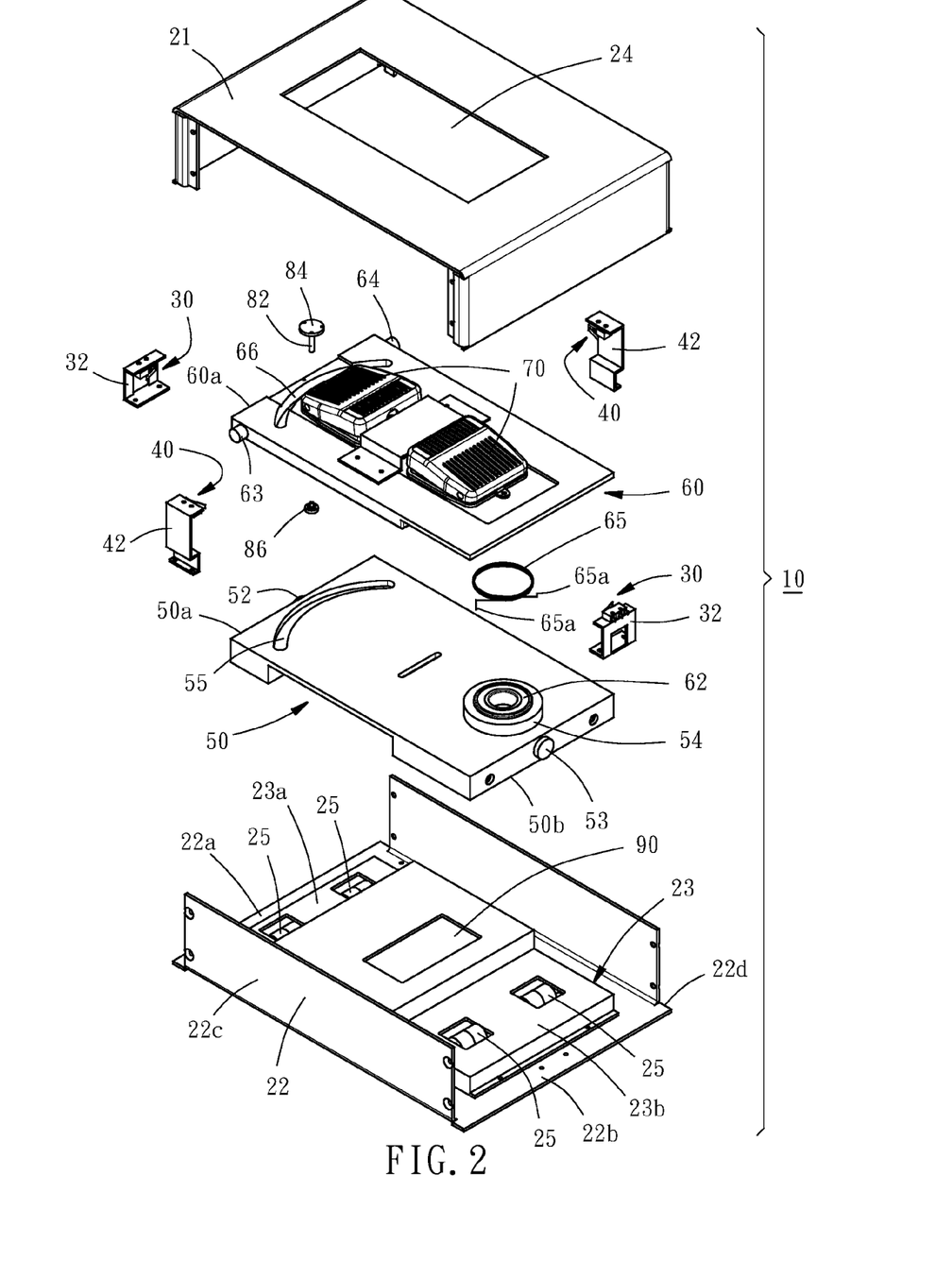
FIG. 2 is an exploded view of the present invention.

Referring to FIG. 1 and FIG. 2, in one embodiment of the present invention, a multidirectional foot controller 10 comprises a base 20, two first position detecting switches 30, two second position detecting switches 40, a first platform 50, a second platform 60, and two pedals 70.

The base 20 has an upper housing 21, a lower housing 22, an third platform 23, and a plurality of rollers 25. The upper housing 21 has a window 24. The lower housing 22 is assembled to the upper housing 21 from below. The third platform 23 is fixed to the top surface of the lower housing 22. The rollers 25 are evenly distributed at the front and rear ends 23a, 23b of the third platform 23.

The first position detecting switches 30 as shown are limit switches that are fixed to the front and rear ends 22a, 22b of the lower housing 22 of the base 20 through two first switch holders 32.

The second position detecting switch 40 as shown are limit switches that are fixed to the left and right sides of the lower housing 22 of the base 20 through two second switch holders 42.

Figure 3:
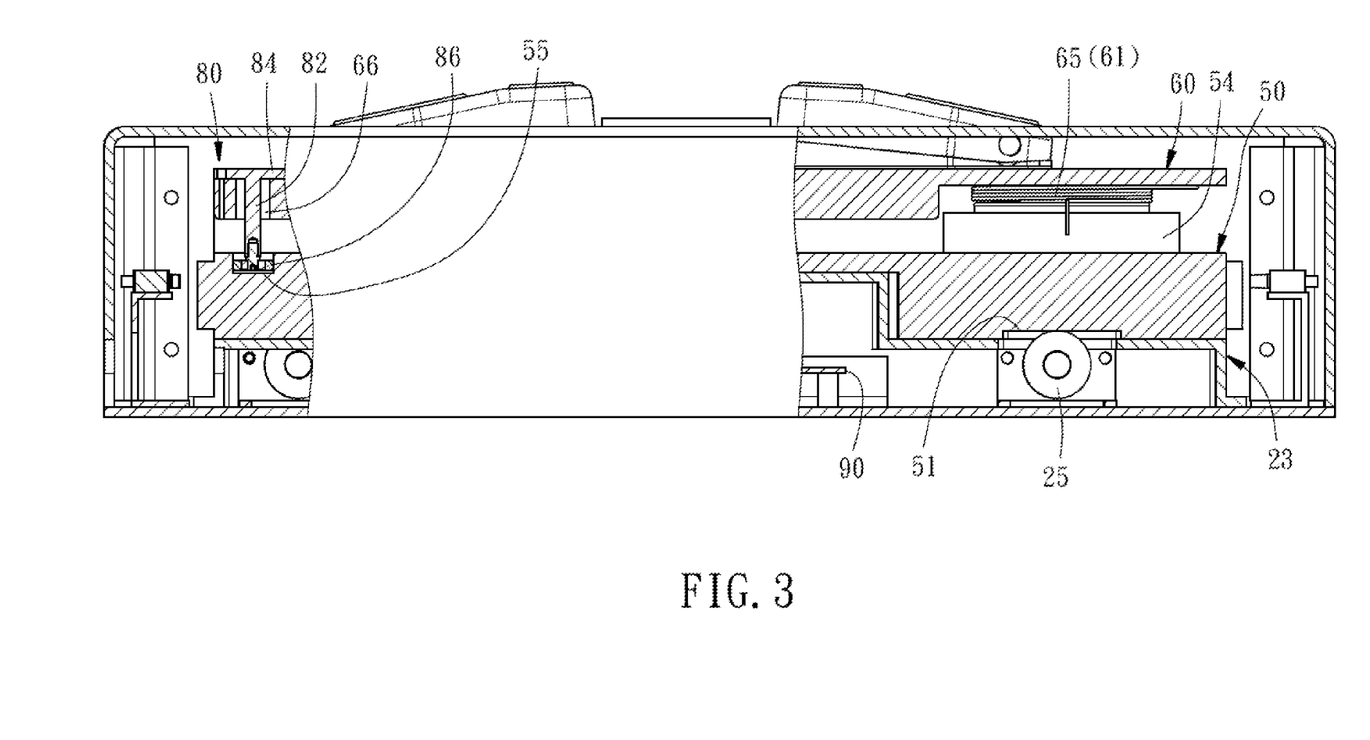
FIG. 3 is a partial, cross-sectional of the present invention.

The first platform 50 is assembled to the top surface of the third platform 23, and, as shown in FIG. 3, the front and rear ends 50a, 50b of the bottom surface of the first platform 50 has two roller tracks 51. Each of the roller tracks 51 accommodates with two rollers 25, so that the first platform 50 are allowed to move forward or backward with respect to the base 20 by means of the rollers 25. Additionally, the front end 50a of the first platform 50 has a front protrusion 52. The rear end of the first platform 50 has a rear protrusion 53 and a first pivot portion 54 near the rear protrusion 53. Each of the front and rear protrusions 52, 53 positionally corresponds to one of the first position detecting switches 30.

The second platform 60 is assembled to the top surface of the first platform 50. The second platform 60 at its bottom surface near its rear end has a second pivot portion 61. The second pivot portion 61 is pivotally connected to the first pivot portion 54 of the first platform 50 through a bearing 62, so that the second platform 60 can on one hand rotate leftward or rightward with respect to the first platform 50 and on the other hand drive the first platform 50 to move forward or backward with respect to the base 20. Moreover, the left and right sides of the second platform 60 are provided with a left protrusion 63 and a right protrusion 64, respectively. Each of the left and right protrusions 63, 64 positionally corresponds to one of the second position detecting switches 40.

For allowing the second platform 60 to automatically return to its original position after rotation, a torsion spring 65 is mounted around the first pivot portion 54 of the second platform 60. As shown in FIG. 2 and FIG. 3, the torsion spring 65 has its two ends connected to the first platform 50 and the second platform 60, respectively, so that the torsion spring 65 provides a returning force to the second platform 60. Also, as shown in FIG. 2 and FIG. 3, the first platform 50 has its front end 50a provided with a lower curved groove 55, and the second platform 60 has its front end 60a provided with an upper curved groove 66. A guiding member 80 is placed in the upper and lower curved grooves 65, 55. The guiding member 80 has a shaft 82, a fixed block 84, and an idler 86. The shaft 82 passes through the upper curved groove 66 of the second platform 60 and the lower curved groove 55 of the first platform 50. The fixed block 84 is connected to the top end of the shaft 82 and is fixed to the top surface of the second platform 60. The idler 86 is rotatably connected to the bottom end of the shaft 82 and rollably abuts against the wall of the lower curved groove 55 of the first platform 50. Thereby, the guiding member 80 moves along the upper and lower curved grooves 65, 55 as the second platform 60 rotates, so as to further ensure stable movement of the second platform 60.

The two pedals 70 are tandem and symmetrically arranged on the top surface of the second platform 60, and are exposed at the window 24 of the upper housing 21 of the base 20, for a user to step.

Furthermore, the disclosed multidirectional foot controller 10 has a circuit board 90 that is fixed to the lower housing 22 of the base 20 and located below the third platform 23. The circuit board 90 is electrically communicated with the pedals 70, the first position detecting switches 30, and the second position detecting switches 40 simultaneously, so as to process the signals from the pedals 70, the first position detecting switches 30, and the second position detecting switches 40, thereby allowing the disclosed multidirectional foot controller 10 to drive a robotic arm (not shown) that in turn drives an endoscope (not shown) under the control of an operating surgeon for minimally invasive surgery.

Figure 4:
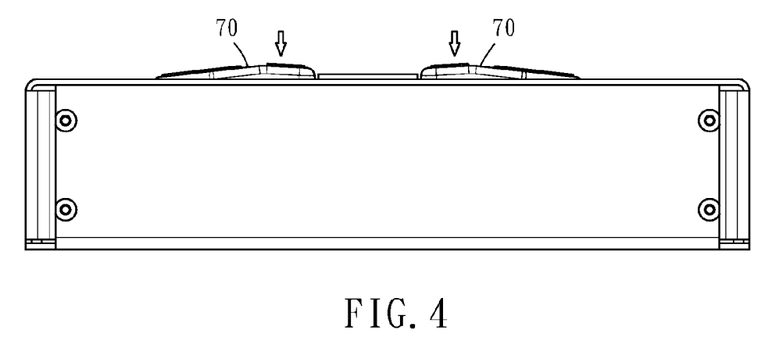
FIG. 4 is a side view of the present invention, showing the tandem pedals are depressant simultaneously.
Figure 5:
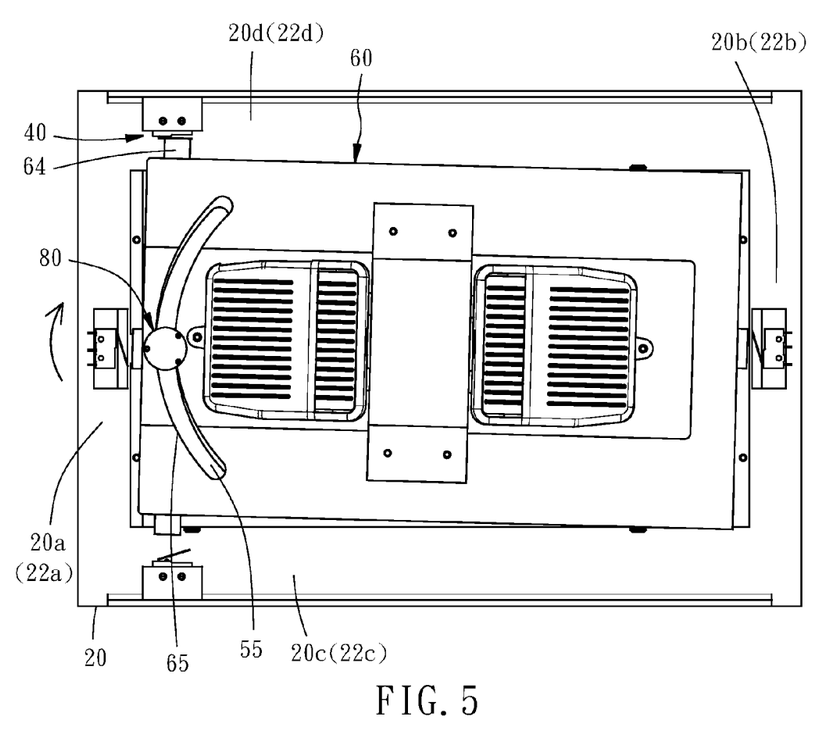
FIG. 5 is a top view of the present invention, showing the second platform rotating rightward.
Figure 6:
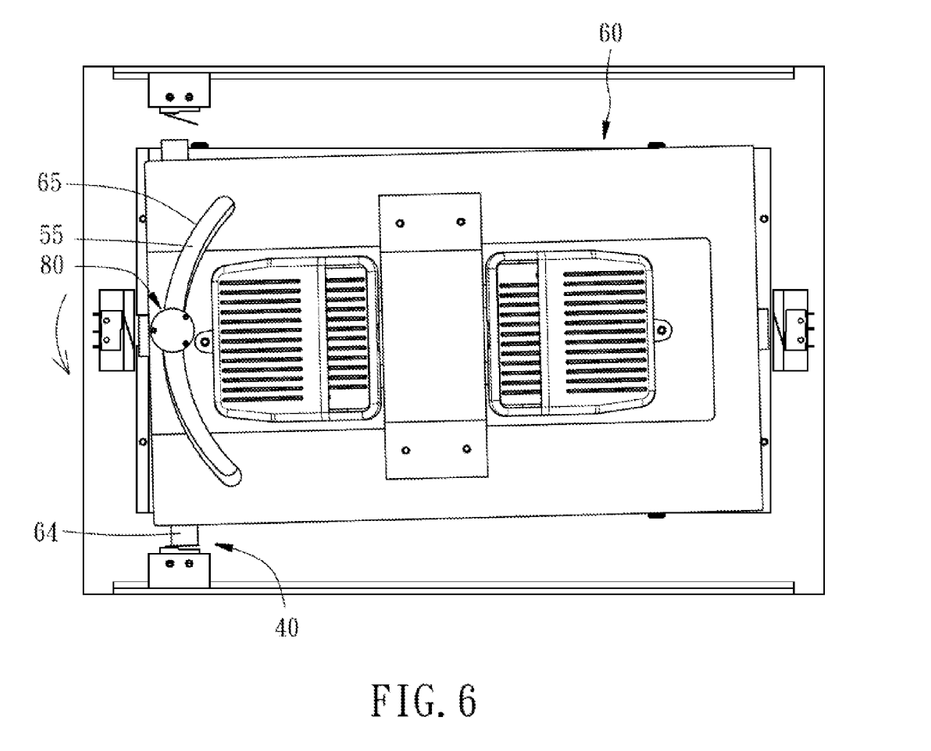
FIG. 6 is similar to FIG. 5 but shows the second platform rotating leftward.
Figure 7:
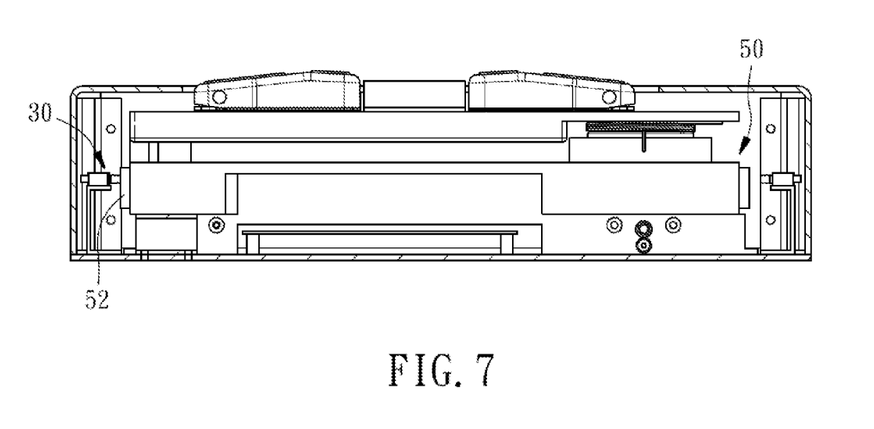
FIG. 7 is a side view of the present invention, showing the first platform moving forward.
Figure 8:
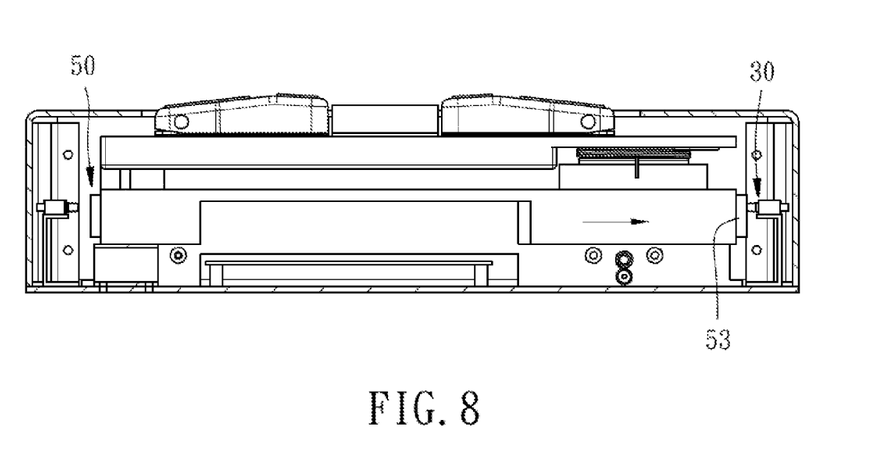
FIG. 8 is similar to FIG. 7 but shows the first platform moving backward.
Figure 9:
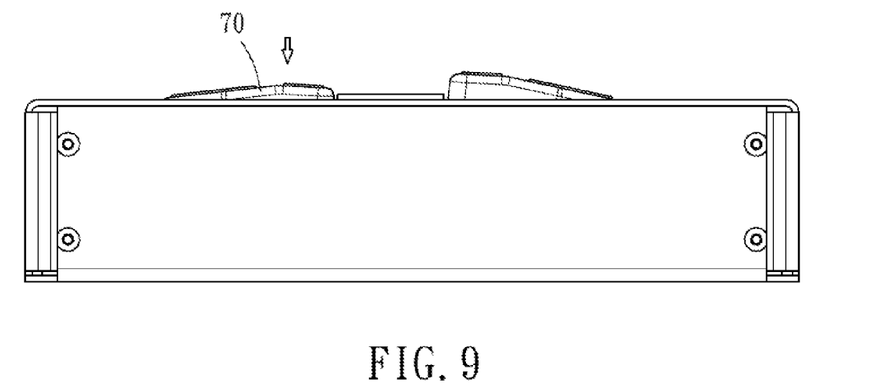
FIG. 9 is a side view of the present invention, showing the front pedal pressed.
Figure 10:
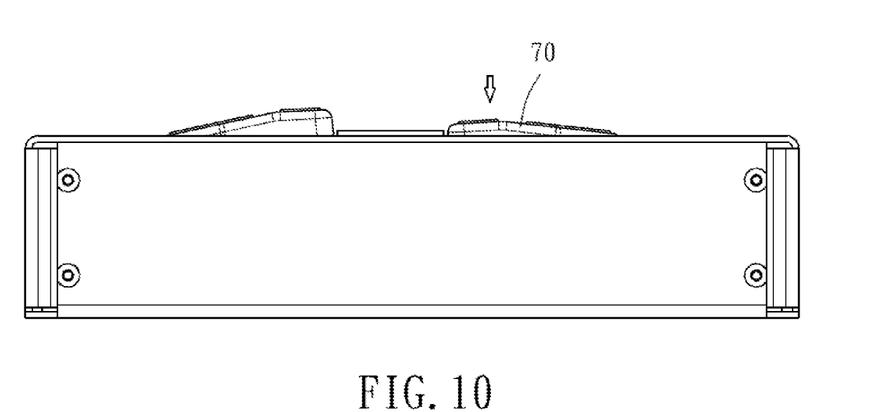
FIG. 10 is similar to FIG. 9 but shows the rear pedal pressed.

In use, the two pedals 70 are simultaneously depressed to turn on the controller (as shown in FIG. 4). Then, for controlling a robotic arm to drive an endoscope to move leftward or rightward, a user may selectively use the two pedals 70 to directly make the second platform 60 rotate leftward or rightward. When the second platform 60 has its left protrusion 63 or right protrusion 64 touching the second position detecting switch 40, as shown in FIG. 5 and FIG. 6, the robotic arm is controlled to make the endoscope move leftward or rightward. When the endoscope reaches the intended site, the left protrusion 63 or the right protrusion 64 of the second platform 60 is operated to leave the second position detecting switch 40 it previously contacted. At this time, the robotic arm stops moving and the placement of the endoscope is finished. On the other hand, for controlling the robotic arm to drive the endoscope to move forward or backward, the user may operate the pedals 70 and in turn the second platform 60 to drive the first platform 50 to move forward or backward. When the front protrusion 52 or the rear protrusion 53 of the first platform 50 touches the first position detecting switch 30, as shown in FIG. 7 and FIG. 8, the robotic arm can be controlled to drive the endoscope to move forward or backward. When the endoscope reaches the intended site, the front protrusion 52 or the rear protrusion 53 of the first platform 50 is moved away from the first position detecting switch 30 it previously contacted, so the robotic arm stops moving and the placement of the endoscope is finished. Moreover, for sizing the field of view of the endoscope through the robotic arm, as shown in FIG. 9 and FIG. 10, the user may release the force he/she applies to one of the pedals 70, meaning that only one of the pedals 70 is depressed. When the endoscope's field of view is well adjusted, the user once again steps on the both pedals 70, so as to further control the first platform 50 and the second platform 60.

To sum up, the disclosed multidirectional foot controller 10 uses the forward and backward movements of the first platform 50, the single-axis rotation of the second platform 60, and the up and down movements of the pedals 70 to provide a multidirectional operation mode. This allows a user to operate an endoscope through a robotic arm more stably, thereby improving working efficiency and operational precision.

What is claimed is:

1. A multidirectional foot controller, comprising:
   a base;
   two first position detecting switches, deposited at front and rear ends of the base, respectively;
   two second position detecting switches, deposited at left and right sides of the base, respectively;
   a first platform, being such installed on a top surface of the base that the first platform is allowed to move forward or backward with respect to the base and is allowed to selectively touch one of the first position detecting switches;
   a second platform, being pivotally installed on a top surface of the first platform that the second platform is allowed to rotate leftward or rightward with respect to the first platform, and allowed to selectively touch one of the second position detecting switches; and two pedals, being such deposited on a top surface of the second platform that the two pedals are tandem arranged;

wherein the base has a lower housing, a fixed platform, and at least two rollers, the fixed platform being assembled to a top surface of the lower housing, the two rollers being deposited at two ends of the fixed platform, the two first position detecting switches being deposited at front and rear ends of the lower housing, the two second position detecting switches being deposited at left and right sides of the lower housing, the first platform being deposited on a top surface of the fixed platform, the first platform having a bottom surface provided with at least two roller tracks, and each of the roller tracks abutting against one said roller.

2. The multidirectional foot controller of claim 1, wherein the base further comprises a circuit board that is fixed to the lower housing and is electrically connected to the two first position detecting switches, the two second position detecting switches, and the two pedals.

3. The multidirectional foot controller of claim 1, wherein the top surface of the first platform has a first pivot portion, and a bottom surface of the second platform has a second pivot portion, in which the first and second pivot portions are pivotally combined through a bearing.

4. The multidirectional foot controller of claim 3, further comprising a torsion spring that is such mounted around the second pivot portion of the second platform, and two ends of the torsion spring are connected to the first platform and the second platform, respectively.

5. The multidirectional foot controller of claim 1, further comprising a guiding member, wherein the first platform has a lower curved groove, and the second platform has an upper curved groove, while the guiding member has a shaft, a fixed block, and an idler, in which the shaft is received in the upper curved groove of the second platform and the lower curved groove of the first platform, and the fixed block is connected to a top end of the shaft and fixed to a top surface of the second platform, while the idler is rotatably connected to a bottom end of the shaft and abuts against a wall of the lower curved groove of the first platform.

6. The multidirectional foot controller of claim 1, wherein the first platform has front and rear ends thereof provide with a front protrusion and a rear protrusion, respectively, and the first platform touches the two first position detecting switches through the front and rear protrusions.

7. The multidirectional foot controller of claim 1, wherein the second platform has left and right sides thereof provided with a left protrusion and a right protrusion, respectively, and the second platform touches the two second position detecting switches through the left and right protrusion.

* * * * *